US009511166B1

(12) United States Patent
Li

(10) Patent No.: US 9,511,166 B1
(45) Date of Patent: Dec. 6, 2016

(54) AROMA DIFFUSER WITH DIRECT DIFFUSION OF ESSENTIAL OIL AND DIFFUSING METHOD THEREOF

(71) Applicant: Puzhen Life Co., Limited, Hong Kong (HK)

(72) Inventor: Dong Sheng Li, Hong Kong (HK)

(73) Assignee: PUZHEN LIFE CO., LIMITED, Hong Kong (HK)

( * ) Notice: Subject to any disclaimer, the term of this patent is extended or adjusted under 35 U.S.C. 154(b) by 0 days.

(21) Appl. No.: 15/073,680

(22) Filed: Mar. 18, 2016

(30) Foreign Application Priority Data

Mar. 2, 2016 (CN) .......................... 2016 1 0119383

(51) Int. Cl.
| | |
|---|---|
| *A62C 5/02* | (2006.01) |
| *A61L 9/14* | (2006.01) |
| *B05B 7/24* | (2006.01) |
| *A61M 11/00* | (2006.01) |
| *B05B 1/34* | (2006.01) |
| *B05B 7/08* | (2006.01) |
| *A61M 11/06* | (2006.01) |
| *A61M 21/00* | (2006.01) |

(52) U.S. Cl.
CPC .............. *A61L 9/145* (2013.01); *A61M 11/002* (2014.02); *A61M 11/06* (2013.01); *A61M 21/00* (2013.01); *B05B 1/34* (2013.01); *B05B 7/0815* (2013.01); *B05B 7/2416* (2013.01); *B05B 7/2429* (2013.01); *A61L 2209/134* (2013.01)

(58) Field of Classification Search
CPC ... A61L 9/145; A61L 2209/134; A61M 11/06; A61M 21/00; A61M 11/002; B05B 7/2416; B05B 7/2429; B05B 7/0815; B05B 1/34

USPC ..... 239/8, 11, 340, 351, 355, 360, 361, 366, 239/368, 369, 69, 338
See application file for complete search history.

(56) References Cited

U.S. PATENT DOCUMENTS

| | | | |
|---|---|---|---|
| 7,913,933 B2 * | 3/2011 | Van Roemburg ..... | B05B 7/0012 239/338 |
| 9,358,557 B2 * | 6/2016 | Young ................... | B05B 7/0012 |
| 2010/0084484 A1 | 4/2010 | Sevy | |

FOREIGN PATENT DOCUMENTS

| | | |
|---|---|---|
| AU | 2005237658 B2 | 11/2005 |
| CN | 2684939 Y | 3/2005 |

(Continued)

OTHER PUBLICATIONS

Search Report issued by the Chinese Patent Office on Mar. 25, 2016.

*Primary Examiner* — Steven J Ganey

(57) ABSTRACT

The present invention relates to an aroma diffuser with direct diffusion of essential oil, and an aroma diffusing method. The aroma diffuser comprises a base, a housing mounted on the base and an electric control element disposed on the housing. An essential oil bottle and a gasification element are also disposed on the housing, a pump element is disposed inside the housing and the open end of the essential oil bottle is connected to the lower end of the gasification element. The pump element is connected to the gasification element and the electric control element respectively and communicates with the gasification element. The gasified essential oil gas may be diffused to ambient air directly, rather than through the housing, the diffusion is fast, and the directly diffused essential oil does not need the dilution of water, greatly raising the efficiency of aromatherapy and meeting people's use requirements.

27 Claims, 10 Drawing Sheets

(56) References Cited

FOREIGN PATENT DOCUMENTS

| | | |
|---|---|---|
| CN | 204972379 U | 1/2016 |
| EP | 1829560 A1 | 9/2007 |
| JP | 04-197261 A | 7/1992 |

* cited by examiner

AROMA DIFFUSER WITH DIRECT DIFFUSION OF ESSENTIAL OIL AND DIFFUSING METHOD THEREOF

CROSS-REFERENCE TO RELATED APPLICATIONS

The present application claims the benefit of Chinese Patent Application No. 201610119383.3 filed on Mar. 2, 2016, the contents of which are hereby incorporated by reference.

TECHNICAL FIELD

The present invention relates to an aroma diffuser, particularly to an aroma diffuser with direct diffusion of essential oil, and an aroma diffusing method.

DESCRIPTION OF THE BACKGROUND

Aroma diffusers make use of the unique charm of fragrance and extend communication from vision and hearing to smell and even deeper layers. Aromatherapy is a fashion, a culture, and a way of spiritual sustenance for people pursuing high-taste life and is suitable for various places, such as: home, and hotel guestrooms, lobbies and corridors.

Following the improvement of people's living standard, more and more people use essential oil to relieve nerves, preserve life, ease tension or soothe the mind. In general, essential oil is classified into single essential oil and compound essential oil. Single essential oil is the essence extracted from a whole plant or a specific location of the plant and typically has rich odor of this plant, a specific efficacy and individual features. Compound essential oil is a mixture of two or more than two essential oils in order to achieve a specific curative effect. These essential oils are mutually coordinated and supplement each other to boost the curative effect.

Current aroma diffusers decompose water containing dissolved essential oil into cold mist through heating or through high frequency oscillation generated by ultrasonic oscillator, or atomize essential oil into gas through an atomizer disposed inside the housing. The mist or gas is diffused into ambient air from the housing and makes the air filled with pleasing fragrance. However, the working device of this aroma diffuser typically is disposed inside the housing. The gas is diffused into ambient air via the fragrance diffusion outlet on the housing. It is prone to the problem of air tightness. Moreover, most part of the gas coming out is water mist. The efficiency is low. The aromatherapy effect might be affected. Further, the working elements are not easily replaced, have a low service life and cannot meet people's use requirements.

Therefore, it is in urgent need of an aroma diffuser with direct diffusion of essential oil.

SUMMARY OF THE INVENTION

The object of the present invention is to overcome the shortcoming of the prior art and provide an aroma diffuser with direct diffusion of essential oil, and an aroma diffusing method.

The object of the present invention is realized in the following way. The aroma diffuser with direct diffusion of essential oil in the present invention comprises a base, a housing mounted on the base and an electric control element disposed on a side face of the housing. It has the following improvements: An essential oil bottle and a gasification element are also disposed on the side face of the housing, a pump element is disposed inside the housing, the open end of the essential oil bottle is connected to the lower end of the gasification element, and the pump element is connected to the gasification element and the electric control element respectively and communicates with the gasification element.

Further, a receiving groove is disposed on a side face of the housing. The essential oil bottle is received in the receiving groove after it is connected to the gasification element. A guide rail and a window are disposed on the upper side wall and bottom wall of the receiving groove respectively. The upper part of the gasification element has a guide slot corresponding to the guide rail. The guide rail matches with the guide slot.

Further, the receiving groove comprises integrally formed upper receiving groove and lower receiving groove. The shape of the upper receiving groove corresponds to the gasification element. The upper end of the upper receiving groove stretches to the upper end face of the housing. The shape of the lower receiving groove corresponds to the essential oil bottle. The essential oil bottle and the gasification element are disposed inside the lower receiving groove and the upper receiving groove respectively after they are connected to each other. A guide rail and a window are disposed on the side wall and bottom wall of the upper receiving groove respectively.

Further, the gasification element comprises a gasification chamber body and a gasification chamber cover snapped onto the gasification chamber body. The upper part of the gasification chamber body has a guide slot corresponding to the guide rail. The lower end of the gasification chamber body is connected to an open end of the essential oil bottle. The right side face of the gasification chamber body is connected to the pump element. The upper end of the gasification chamber cover has a fragrance diffusion outlet.

Further, the gasification chamber body comprises a gasification chamber, an essential oil nozzle, an oil conduit, an air nozzle and a swivel joint. The gasification chamber is connected to the open end of the essential oil bottle. The essential oil nozzle and the oil conduit are disposed at the lower end of the gasification chamber body. The upper end of the essential oil nozzle is located inside the gasification chamber and communicates with the gasification chamber. The lower end of the essential oil nozzle is connected to the upper end of the oil conduit and communicates with the upper end of the oil conduit. The lower end of the oil conduit stretches into the essential oil bottle, with its lower end face close to the bottom surface of the essential oil bottle, and communicates with the essential oil bottle. The swivel joint is disposed on the right side face of the gasification chamber body and connected to and communicates with the pump element. The air nozzle is disposed between the gasification chamber and the swivel joint and communicates with them respectively. The air nozzle is disposed in a tilted manner, with one side close to the upper end of the essential oil nozzle.

Further, the air nozzle comprises an air nozzle through-hole. The air nozzle communicates with the gasification chamber and the swivel joint respectively through the air nozzle through-hole. The longitudinal central cross-section of the air nozzle through-hole has an upper edge and lower edge, where:

The intersection between the upper edge and the extension line of the upper edge is A;

The intersection between the extension line of the upper edge and the centerline of the essential oil nozzle is C;

The intersection between the extension line of the lower edge and the centerline of the essential oil nozzle is D;

The distance from intersection A to intersection C is F;

The distance from intersection C to intersection D is H;

The distance from intersection C to the end face of the essential oil nozzle is M;

The included angle between the extension line of the upper edge and the centerline of the essential oil nozzle is Q;

The length of F is 0.3 mm-10 mm, the length of M is 0-2H, and the included angle Q is an acute angle.

Further, the vertical distance from the extension line of the upper edge to the extension line of the lower edge is G, the relations among G, H and Q are $\cos(90-Q)=G/H$ and the length of M is $0-2G/\cos(90-Q)$.

Further, the inner diameter of the air nozzle through-hole and the essential oil nozzle is 0.2-2.0 mm.

Further, the gasification chamber body further comprises a vortex body. The vortex body comprises a lower vortex body and an upper vortex body. The lower vortex body and the upper vortex body are both disposed inside the gasification chamber. The lower end of the lower vortex body has an air inflow reflux hole. The lower vortex body communicates with the gasification chamber through the air inflow reflux hole. The lower end of the upper vortex body is disposed on the upper end of the lower vortex body. The upper vortex body communicates with the lower vortex body. The upper end of the upper vortex body has a fragrance outlet. The upper end of the upper vortex body is connected to the gasification chamber cover. A fragrance channel is formed between the upper vortex body and the gasification chamber cover. The upper vortex body communicates with the fragrance channel through the fragrance outlet. The fragrance channel communicates with the fragrance diffusion outlet.

Further, the pump element comprises a front housing, a rear housing connected to the front housing in a snapped manner, a pump body, a sealing gasket and an airflow reversing nozzle body. The pump body is disposed inside a cavity enclosed by the front housing and the rear housing. The pump body is connected to the electric control element. The upper end and the lower end of the pump body have an air outlet and an air inlet respectively. The sealing gasket is disposed on the upper end of the pump body and communicates with the air outlet. The airflow reversing nozzle body is disposed on the sealing gasket in a sleeved manner, communicates with the sealing gasket and has an airflow reversing nozzle. The airflow reversing nozzle passes through the front housing and the window in turn, connects the swivel joint in an abutted manner and communicates with the swivel joint.

Further, the bottom surface of the gasification chamber has an annular flange inlaid in the open end of the essential oil bottle, and the gasification chamber communicates with the open end of the essential oil bottle through the annular flange.

Further, a seal ring is disposed between the annular flange and the open end of the essential oil bottle.

Further, the lower end of the gasification chamber body comprises a first thread, the open end of the essential oil bottle comprises a second thread matching the first thread, and the first thread is connected to the second thread.

Further, a cushion is disposed between the pump body and the front housing and between the pump body and the rear housing respectively.

Further, the electric control element comprises a circuit board, a knob holder, a pump flow regulating knob, a timing knob and an intermittent working time setting knob. The pump flow regulator, the timer and the intermittent working time setter are disposed on the circuit board. The circuit board is connected to the pump body. The knob holder is fixed on the circuit board and disposed on the pump flow regulator, the timer and the intermittent working time setter in a sleeved manner. The pump flow regulating knob, the timing knob and the intermittent working time setting knob are all disposed on the knob holder, and connected to the pump flow regulator, the timer and the intermittent working time setter through the connecting shaft inside the knob holder.

Further, the pump body comprises an upper housing, a support, a middle housing, a lower housing, an air outlet, a motor and an air inlet. The upper housing, the support, the middle housing, the lower housing and the motor are installed in sequence from top to bottom. The air outlet is located on the upper end of the upper housing. The air inlet is located on a side face of the lower housing. The motor is connected to the circuit board. A sealing gasket is disposed on the upper end of the upper housing and communicates with the air outlet. A valve is disposed inside the support. A piston and an eccentric gear are disposed inside the middle housing from top to bottom. One end of the piston clings to the bottom surface of the support and another end is fixed on the eccentric gear. A connecting rod is disposed inside the lower housing. One end of the connecting rod is connected to the eccentric gear through a spindle and another end is connected to a motor.

The present invention further provides an aroma diffuser, comprising:

A base;

A housing mounted on the base;

An essential oil bottle for accommodating essential oil;

A gasification element for gasifying essential oil;

A pump element communicating with the gasification element;

An electric control element for controlling the pump element;

The open end of the essential oil bottle is connected to and communicates with the lower end of the gasification element. The pump element is connected to the gasification element and the electric control element respectively.

Further, the gasification element comprises an air nozzle and an essential oil nozzle. The air nozzle comprises an air nozzle through-hole. The longitudinal central cross-section of the air nozzle through-hole has an upper edge and a lower edge, where:

The intersection between the extension line of the upper edge and the centerline of the essential oil nozzle is C;

The intersection between the extension line of the lower edge and the centerline of the essential oil nozzle is D;

The distance from intersection C to intersection D is H;

The included angle between the extension line of the upper edge and the centerline of the essential oil nozzle is Q;

The vertical distance from the extension line of the upper edge to the extension line of the lower edge is G;

The distance from intersection C to the end face of the essential oil nozzle is M;

Where: the length of M is 0-2H and the included angle Q is an acute angle;

The relations among G, H and Q are $\cos(90-Q)=G/H$;

The positional relation between the air nozzle and the essential oil nozzle may be defined with Formula $\cos(90-Q)=G/H$.

Further, the included angle Q is 60-90°.

Further, the intersection between the upper edge and the extension line of the upper edge is A. The distance from intersection A to intersection C is F. The length of F is 0.3 mm-10 mm.

Further, the intersection between the upper edge and the extension line of the upper edge is A. The distance from intersection A to intersection C is F. The length of F is 0.5 mm-1.5 mm.

Further, the inner diameter of the air nozzle through-hole and essential oil nozzle is 0.4-0.8 mm.

The present invention further provides an aroma diffusing method, comprising:

Providing an aroma diffuser, comprising a housing, an essential oil bottle, a gasification element, a pump element and an electric control element;

Under action of the electric control element, importing ambient air into the air nozzle of the gasification element through the pump body of the pump element and forming jet stream;

Spraying the jet stream above the essential oil nozzle of the gasification element via an air nozzle to form negative pressure so as to suck liquid essential oil out from the essential oil bottle and gasify the liquid essential oil into essential oil gas;

Diffusing essential oil gas to ambient air through a fragrance diffusion outlet of the gasification element;

In a further embodiment, the aroma difussing method comprising: regulating flow and working time of the pump body of the pump element according to actual need to achieve the required oil consumption and working time.

In a further embodiment, the aroma difussing method comprising: collecting the essential oil gas which becomes liquid essential oil when it collides with the inner wall of the gasification chamber of the gasification element to the essential oil bottle.

In a further embodiment, the aroma difussing method comprising: forming the essential oil gas into vortex airstream through the lower vortex body and the upper vortex body of the gasification element, exporting the airstream out to the fragrance channel of the gasification element, and then diffusing essential oil gas to ambient air through a fragrance diffusion outlet of the gasification element.

Further, the air nozzle comprises an air nozzle through-hole. The longitudinal central cross-section of the air nozzle through-hole has an upper edge and a lower edge, where:

The intersection between the extension line of the upper edge and the centerline of the essential oil nozzle is C;

The intersection between the extension line of the lower edge and the centerline of the essential oil nozzle is D;

The distance from intersection C to intersection D is H;

The included angle between the extension line of the upper edge and the centerline of the essential oil nozzle is Q;

The vertical distance from the extension line of the upper edge to the extension line of the lower edge is G;

The distance from intersection C to the end face of the essential oil nozzle is M;

Where: the length of M is 0-2H and the included angle Q is an acute angle;

The relations among C, H and Q are $\cos(90-Q)=G/H$;

The positional relation between the air nozzle and the essential oil nozzle may be defined with Formula $\cos(90-Q)=G/H$.

Further, the intersection between the upper edge and the extension line of the upper edge is A. The distance from intersection A to intersection C is F. The length of F is 0.3 mm-10 mm.

Compared with the prior art, the present invention has the following beneficial effect: in the present invention, an essential oil bottle and a gasification element are disposed on a side face of the housing, the gasified essential oil gas may be diffused to ambient air directly, rather than through the housing, the diffusion is fast, and the directly diffused essential oil does not need the dilution of water, greatly raising the efficiency of aromatherapy. Further, the base is mounted on the housing and the pump element is disposed inside the housing. They can be easily replaced, installed and maintained and conveniently used and have desirable sealing performance. The aroma diffuser features high safety, high control rate of essential oil volatilization and long service life and significantly meets people's use requirements.

Figure 1:
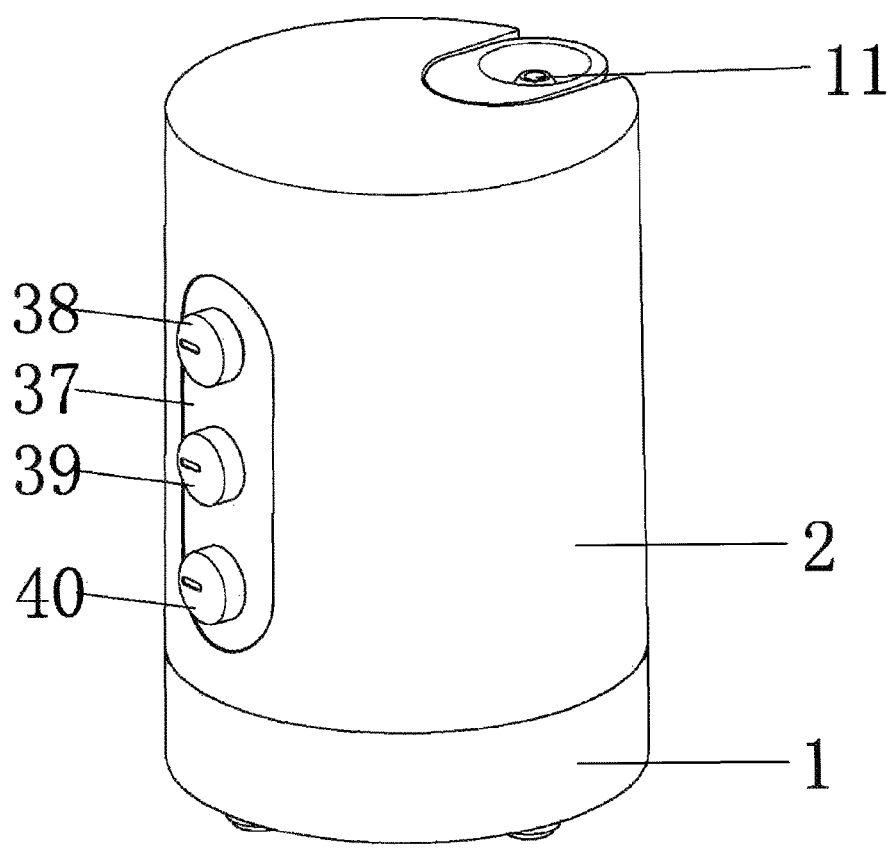
FIG. 1 is a three-dimensional structural schematic 1 of an aroma diffuser with direct diffusion of essential oil in the present invention.
Figure 2:
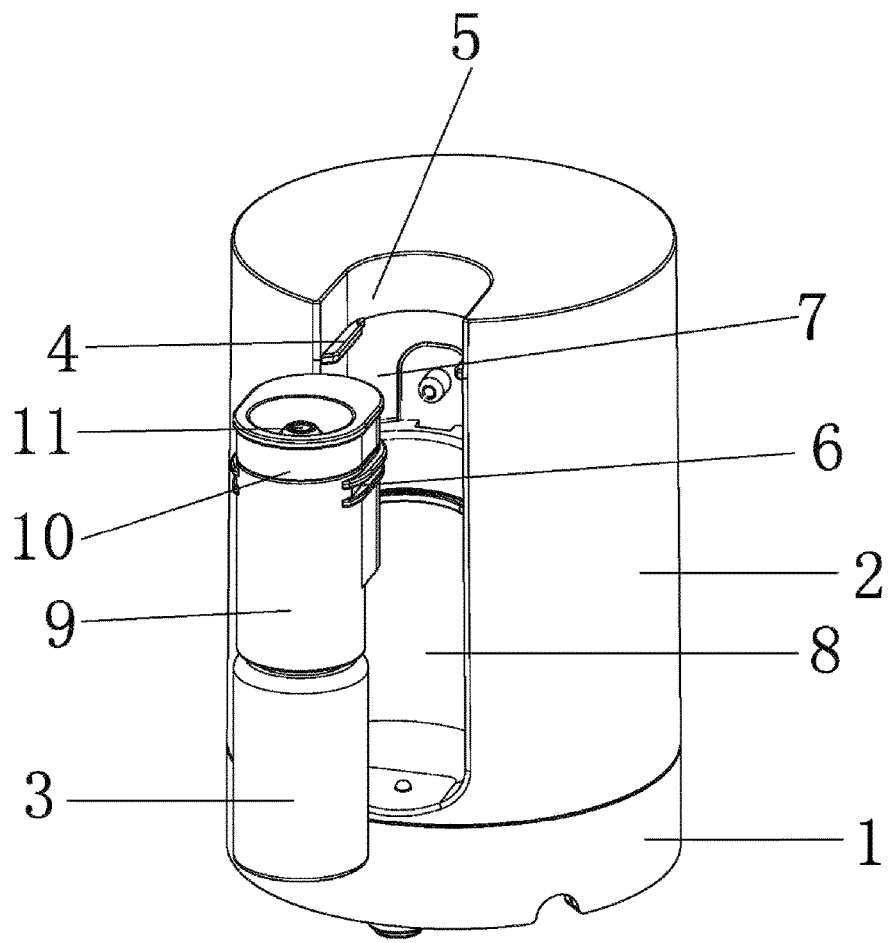
FIG. 2 is a three-dimensional structural schematic 2 of an aroma diffuser with direct diffusion of essential oil in the present invention.
Figure 3:
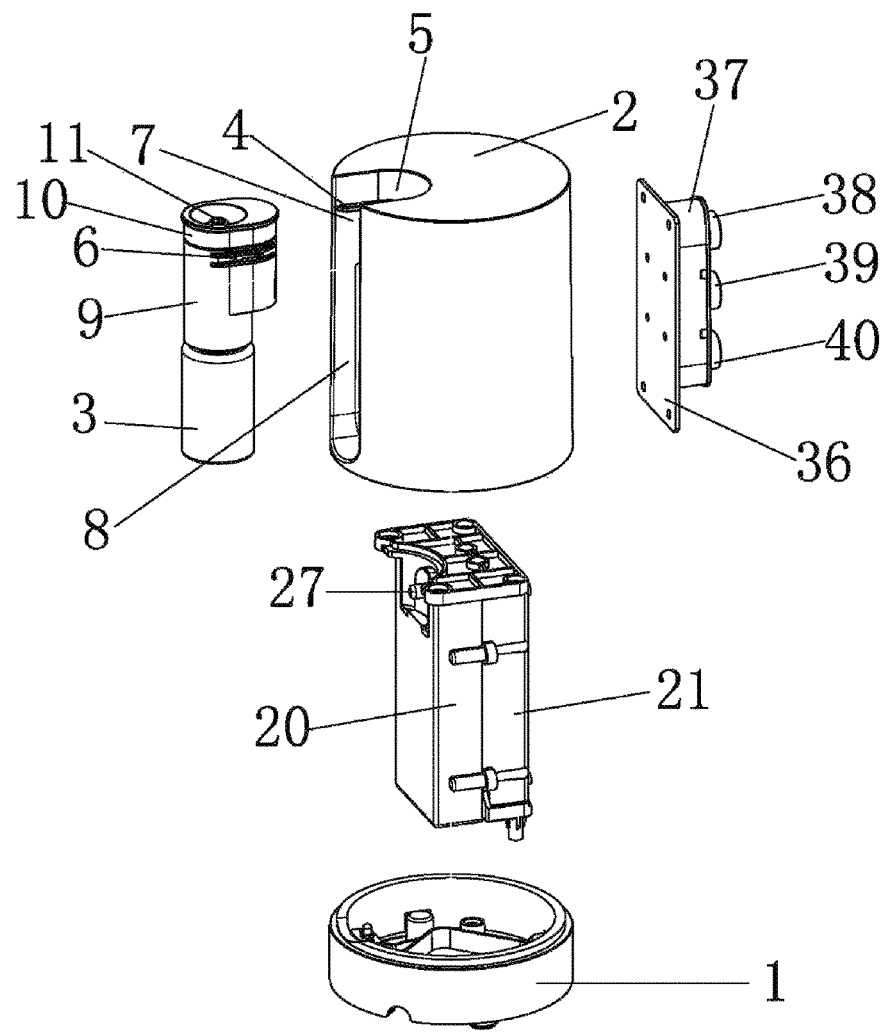
FIG. 3 is an exploded schematic of an aroma diffuser with direct diffusion of essential oil in the present invention.

Where: 1, base; 2, housing; 3, essential oil bottle; 4, guide rail; 5, window; 6, guide slot; 7, upper receiving groove; 8, lower receiving groove; 9, gasification chamber body; 10, gasification chamber cover; 11, fragrance diffusion outlet; 12, gasification chamber; 13, essential oil nozzle; 14, oil conduit; 15, air nozzle; 16, swivel joint; 17, lower vortex body; 18, upper vortex body; 19, fragrance channel; 20, front housing; 21, rear housing; 22, pump body; 23, sealing gasket; 24, airflow reversing nozzle body; 25, air outlet; 26, air inlet; 27, airflow reversing nozzle; 28, annular flange; 29, seal ring; 30, air nozzle through-hole; 31, upper edge; 32, lower edge; 33, extension line of the upper edge; 34, extension line of the lower edge; 35, cushion; 36, circuit board; 37, knob holder; 38, pump flow regulating knob; 39, timing knob; 40, intermittent working time setting knob; 41, pump flow regulator; 42, timer; 43, intermittent working time setter; 44, connecting shaft; 45, upper housing; 46, support; 47, middle housing; 48, lower housing; 49, motor; 50, valve; 51, piston; 52, eccentric gear; 53, connecting rod; 54, spindle.

DETAILED DESCRIPTION OF PREFERRED EMBODIMENTS

Below the present invention will be further described by referring to the accompanying drawings and embodiments.

As shown in FIG. 1, FIG. 2, FIG. 3 and FIG. 4, the present invention discloses an aroma diffuser with direct diffusion of essential oil, comprising a base 1, a housing 2 mounted on the base 1 and an electric control element disposed on the housing 2. An essential oil bottle 3 and a gasification element are also disposed on the housing 2. Single essential oil or compound essential oil may be put in the essential oil bottle 3. A pump element is disposed inside the housing 2. The open end of the essential oil bottle 3 is connected to and communicates with the lower end of the gasification element. The pump element is connected to the gasification element and the electric control element respectively and communicates with the gasification element. In this embodiment, the housing 2 is in a cylindrical shape or in other shapes. In the present invention, an essential oil bottle 3 and a gasification element are disposed on a side face of the housing 2, the gasified essential oil gas may be diffused to ambient air directly, rather than through the housing 2, the diffusion is fast and the efficiency of aromatherapy is raised greatly. Further, the base 1 is mounted on the housing 2 and the pump element is disposed inside the housing 2. They can be easily replaced, installed and maintained and conveniently used and have desirable sealing performance.

Specifically, in this embodiment, a receiving groove is disposed on a side face of the housing 2, the essential oil bottle 3 is received in the receiving groove after it is connected to the gasification element, a guide rail 4 and a window 5 are disposed on an upper side wall and bottom wall of the receiving groove respectively, the upper part of the gasification element has a guide slot 6 corresponding to the guide rail 4, and the guide rail 4 matches the guide slot 6. In this way, the gasification element and the essential oil bottle 3 can be easily installed and disassembled, liquid essential oil can be easily filled into the essential oil bottle 3 and the use is very convenient.

Further, the receiving groove comprises integrally formed upper receiving groove 7 and lower receiving groove 8. The shape of the upper receiving groove 7 corresponds to the gasification element. The upper end of the upper receiving groove 7 stretches to the upper end face of the housing 2. The shape of the lower receiving groove 8 corresponds to the essential oil bottle 3. The essential oil bottle 3 and the gasification element are disposed inside the lower receiving groove 8 and the upper receiving groove 7 respectively after they are connected to each other. A guide rail 4 and a window 5 are disposed on the side wall and bottom wall of the upper receiving groove 7 respectively. It is convenient for placement of the essential oil bottle 3 and the gasification element. The overall structure is compact and artistic.

Figure 4:
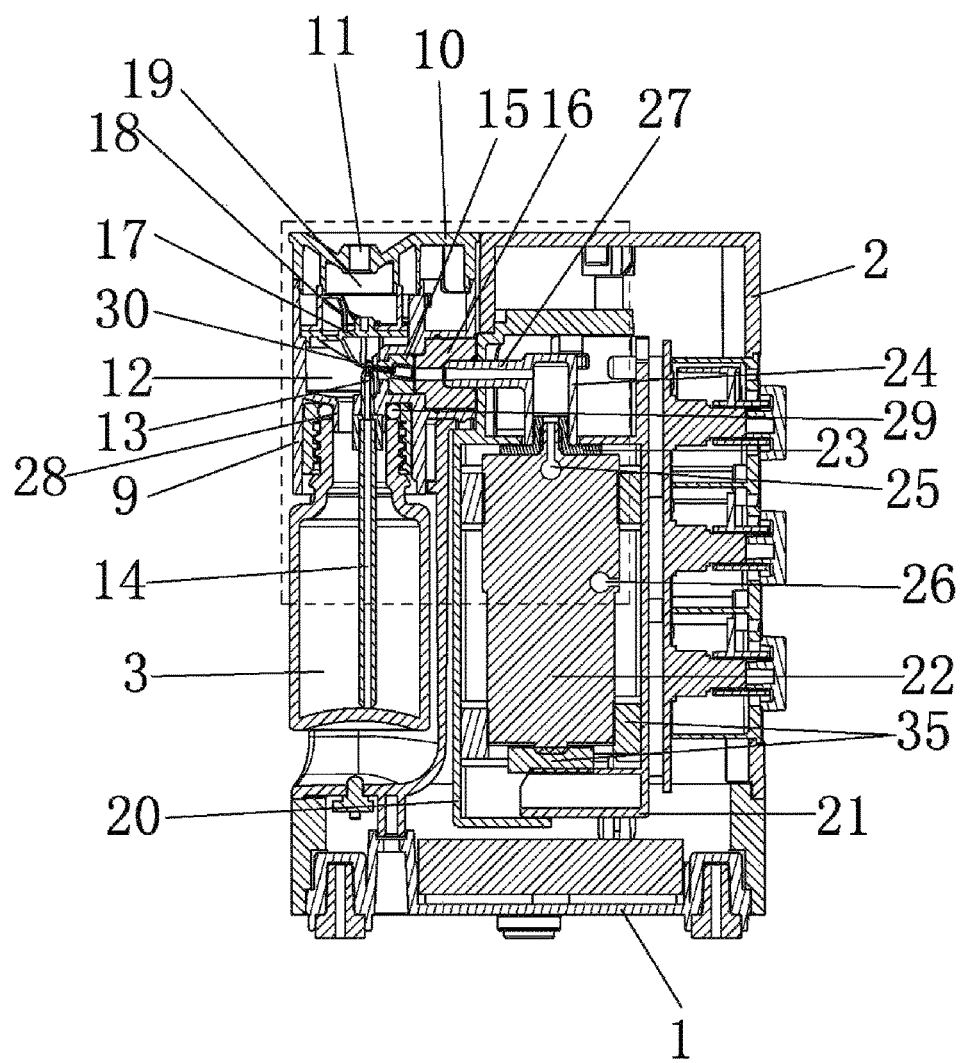
FIG. 4 is a sectional schematic of an aroma diffuser with direct diffusion of essential oil in the present invention.
Figure 5:
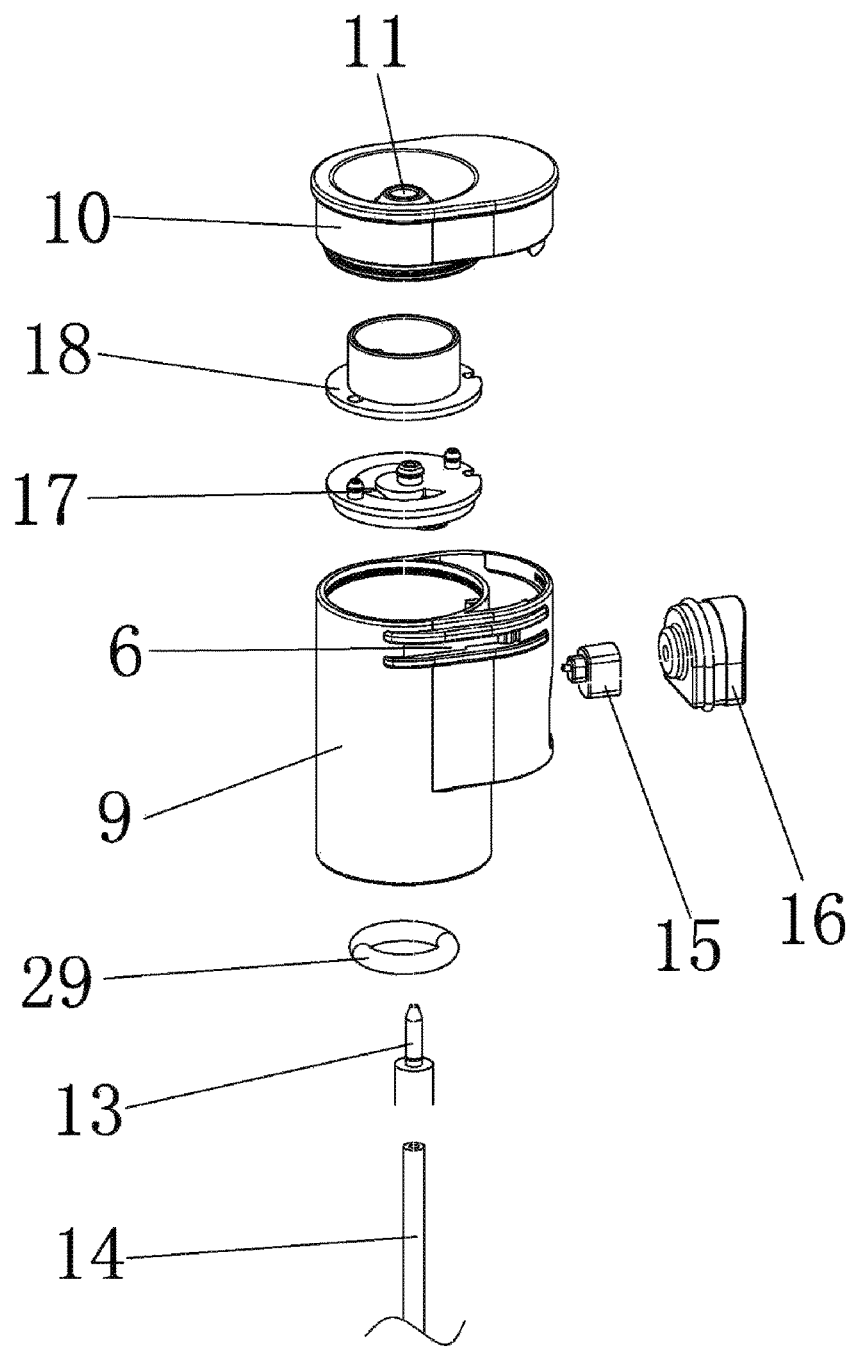
FIG. 5 is an exploded schematic of a gasification element in the present invention.

As shown in FIG. 4 and FIG. 5, in this embodiment, the gasification element comprises a gasification chamber body 9 and a gasification chamber cover 10 snapped into the gasification chamber body 9. The upper part of the gasification chamber body 9 has a guide slot 6 corresponding to the guide rail 4. The lower end of the gasification chamber body 9 is connected to the open end of the essential oil bottle 3. The right side face of the gasification chamber body 9 is connected to the pump element. The upper end of the gasification chamber cover 10 has a fragrance diffusion outlet 11. The fragrance diffusion outlet 11 is directly exposed to the ambient. The gasified essential oil gas may be directly diffused to the ambient air via the fragrance diffusion outlet 11. The diffusion speed and efficiency are high.

Specifically, the gasification chamber body 9 comprises a gasification chamber 12, an essential oil nozzle 13, an oil conduit 14, an air nozzle 15 and a swivel joint 16. The gasification chamber 12 communicates with the open end of the essential oil bottle 3. The essential oil nozzle 13 and the oil conduit 14 are disposed at the lower end of the gasification chamber body 9. The upper end of the essential oil nozzle 13 is located inside the gasification chamber 12 and communicates with the gasification chamber 12. The lower end of the essential oil nozzle 13 is connected to and communicates with the upper end of the oil conduit 14. The lower end of the oil conduit 14 stretches into the essential oil bottle 3, clings to the bottom surface of the essential oil bottle 3 and communicates with the essential oil bottle 3. The swivel joint 16 is disposed on the right side face of the gasification chamber body 9 and is connected to and communicates with the pump element. The air nozzle 15 is disposed between the gasification chamber 12 and the swivel joint 16, communicates with the gasification chamber 12 and the swivel joint 16 respectively and is disposed in a tilted manner, with one side close to the upper end of the essential oil nozzle 13.

Figure 6:
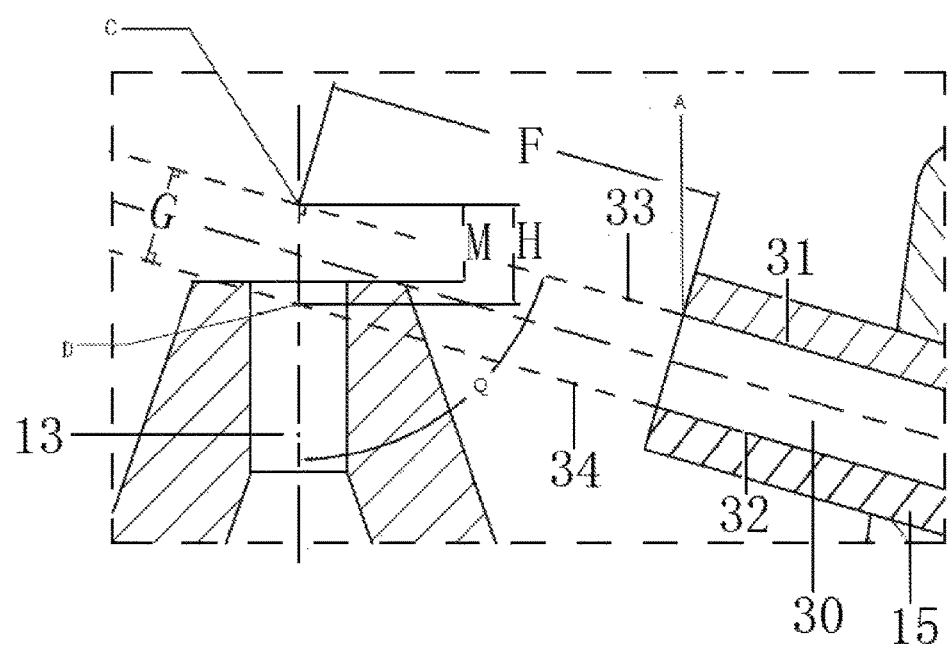
FIG. 6 is a partial enlarged view of an essential oil nozzle and an air nozzle in the present invention.

Further, as shown in FIG. 6, the air nozzle 15 comprises an air nozzle through-hole 30. The air nozzle 15 communicates with the gasification chamber 12 and the swivel joint 16 through the air nozzle through-hole 30. The longitudinal central cross-section of the air nozzle through-hole 30 has an upper edge 31 and a lower edge 32, where:

The intersection between the upper edge 31 and the extension line 33 of the upper edge is A;

The intersection between the extension line 33 of the upper edge and the centerline of the essential oil nozzle 13 is C;

The intersection between the extension line 34 of the lower edge and the centerline of the essential oil nozzle 13 is D;

The distance from intersection A to intersection C is F;

The distance from intersection C to intersection D is H;

The distance from intersection C to the end face of the essential oil nozzle 13 is M;

The included angle between the extension line 33 of the upper edge and the centerline of the essential oil nozzle 13 is Q;

The length of F is 0.3 mm-10 mm, the length of M is 0-2H and the included angle Q is an acute angle.

Further, the vertical distance from the extension line 33 of the upper edge to the extension line 34 of the lower edge is Q the relations among G, H and Q are $\cos(90-Q)=G/H$, and the length of M is $0\text{-}2G/\cos(90-Q)$.

Further, The inner diameter of the air nozzle through-hole 30 and the essential oil nozzle 13 is 0.2-2.0 mm, preferably 0.4 mm-0.8 mm.

The setting of the relative positions of the air nozzle 15 and the essential oil nozzle 13 enables the jet stream sprayed out from the air nozzle 15 to form a zone of negative pressure above the essential oil nozzle 13 so that the oil conduit 14 can suck liquid essential oil out from the essential oil bottle 3 and spray it into the gasification chamber 12 via the essential oil nozzle 13. Meanwhile, the jet stream can gasify the liquid essential oil sprayed from the essential oil nozzle 13 into tiny particles, which will become essential oil gas, thereby completing gasification process, assuring gasification efficiency and achieving high safety.

Further, the gasification chamber body further comprises a vortex body. The vortex body comprises a lower vortex body 17 and an upper vortex body 18. The lower vortex body 18 and the upper vortex body 18 are both disposed inside the gasification chamber 12. The lower end of the lower vortex body 17 has an air inflow reflux hole. In this embodiment, there are two air inflow reflux holes. The lower vortex body 17 communicates with the gasification chamber 12 through the air inflow reflux holes. The lower end of the upper vortex body 18 is disposed on the upper end of the lower vortex body 17. The upper vortex body 18 communicates with the lower vortex body 17. The upper end of the upper vortex body 18 has a fragrance outlet and is connected to the gasification chamber cover 10. A fragrance channel 19 is formed between the upper vortex body 18 and the gasification chamber cover 10. The upper vortex body 18 communicates with the fragrance channel 19 through the fragrance outlet. The fragrance channel 19 communicates with the fragrance diffusion outlet 11.

When passing above the essential oil nozzle 13, the jet stream sprayed from the air nozzle 15 will form negative pressure above the essential oil nozzle 13. At the moment, the oil conduit 14 sucks the liquid essential oil out from the essential oil bottle 3 and sprays it into the gasification chamber 12 via the essential oil nozzle 13. Meanwhile, the jet stream sprayed from the air nozzle 15 can gasify the liquid essential oil sprayed from the essential oil nozzle 13 into tiny particles, which will become essential oil gas. When essential oil gas collides with the inner wall of the gasification chamber 12, part of it will become liquid and flow back to the essential oil bottle 3, while the remaining part of the essential oil gas flows through the lower vortex body 17 and the upper vortex body 18 via the air inflow reflux hole, enters the fragrance channel 19 via the fragrance outlet after it forms vortex gas, and then is diffused into the ambient air from the fragrance diffusion outlet 11, to make the ambient air full of pleasant fragrance.

Further, the bottom surface of the gasification chamber 12 has an annular flange 28, inlaid in the open end of the essential oil bottle 3. The gasification chamber 12 communicates with the essential oil bottle 3 through the annular flange 12. In this embodiment, a seal ring 29 is disposed between the annular flange 12 and the essential oil bottle 3. When part of the essential oil gas collides with the inner wall of the gasification chamber 12, it becomes liquid essential oil and flows back to the essential oil bottle 3 so that it can be used cyclically without waste, reducing cost. Further, it has good sealing performance and can effectively prevent volatilization of essential oil.

Further, the lower end of the gasification chamber body 9 has a first thread, i.e.: internal thread, the open end of the essential oil bottle 3 has a second thread, i.e.: external thread, matching the first thread, and the first thread is connected to the second thread to make for disassembly of the essential oil bottle and operation and achieve desirable sealing performance.

Figure 7:
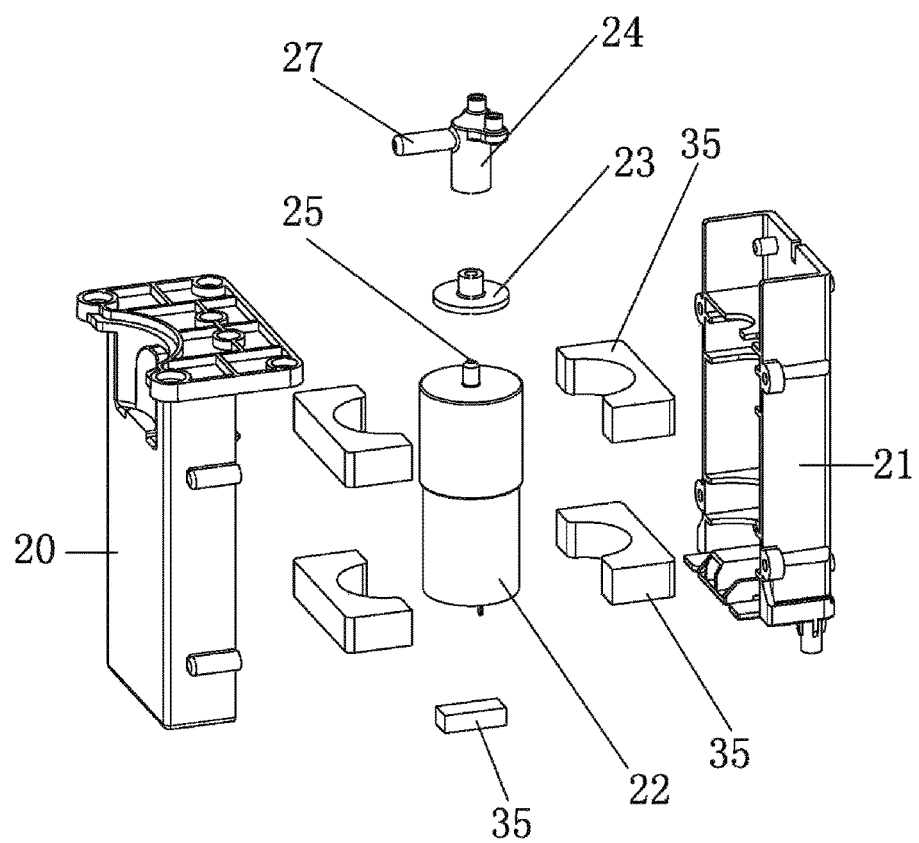
FIG. 7 is an exploded schematic of a pump element in the present invention.

As shown in FIG. 7, in this embodiment, the pump element comprises a front housing 20, a rear housing 21 connected to the front housing 20 in a snapped manner, a pump body 22, a sealing gasket 23 and an airflow reversing nozzle body 24. The pump body 22 is disposed in a cavity enclosed by the front housing 20 and the rear housing 21 and connected to the electric control element. The upper end and lower end of the pump body 22 have an air outlet 25 and an air inlet 26 respectively. The sealing gasket 23 is disposed on the upper end of the pump body 22 and communicates with the pump body 22 through the air outlet 25. The airflow reversing nozzle body 24 is disposed on the sealing gasket 23 in a sleeved manner, communicates with the sealing gasket 23 and has an airflow reversing nozzle 27. The airflow reversing nozzle 27 passes the front housing 20 and a window 5 in turn, is connected to the swivel joint 16 in a butted manner and communicates with the swivel joint 16. Ambient air enters the pump body 22 via the air inlet 26, then enters the swivel joint 16 from the air outlet 25 via the sealing gasket 23, the airflow reversing nozzle body 24 and the airflow reversing nozzle 27 in turn, and completes gasification process through the air nozzle 15. The operation is convenient.

Further, a cushion 35 is disposed between the pump body 22 and the front housing 20 and between the pump body 22 and the rear housing 21 respectively to play a buffer role and lengthen the service life of the components.

Figure 8:
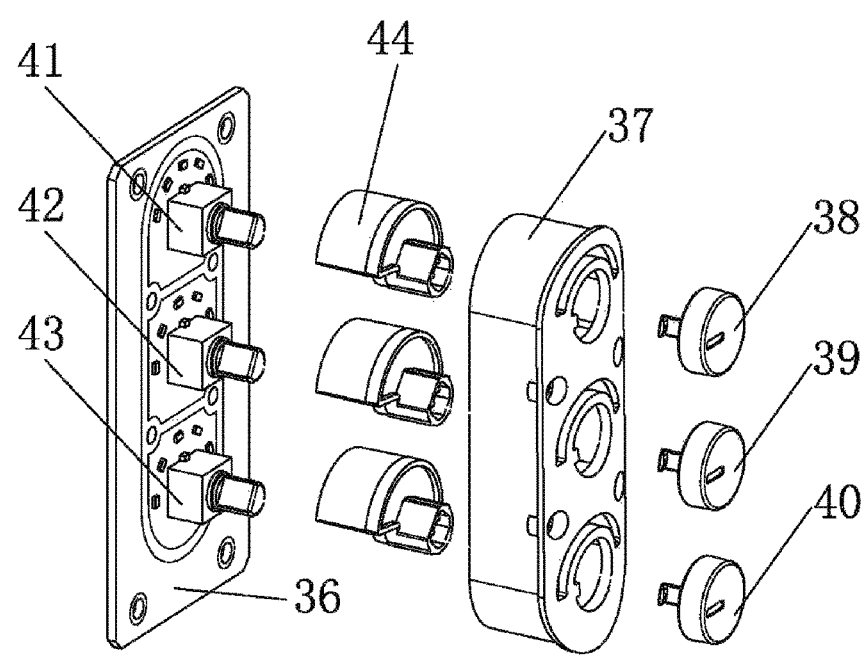
FIG. 8 is an exploded schematic of an electric control element in the present invention.

As shown in FIG. 8, in this embodiment, the electric control element comprises a circuit board 36, a knob holder 37, a pump flow regulating knob 38, a timing knob 39 and an intermittent working time setting knob 40. A pump flow regulator 41, a timer 42 and an intermittent working time setter 43 are disposed on the circuit board 36. The circuit board 36 is connected to the pump body 22. The pump flow regulating knob 38 is intended to regulate the air inflow of the pump body 22, thereby indirectly controlling the flow of liquid essential oil. The timing knob 39 is intended to set working time. The intermittent working time setting knob 40 is intended to set intermittent working time. Oil consumption and working time or intermittent working time may be set according to the actual need. The knob holder 37 is fixed on the circuit board 36 and disposed on the pump flow regulator 41, the timer 42 and the intermittent working time setter 43 in a sleeved manner. The pump flow regulating knob 38, the timing knob 39 and the intermittent working time setting knob 40 are all disposed on the knob holder 37 and connected to the pump flow regulator 41, the timer 42 and the intermittent working time setter 43 respectively through the connecting shaft 44 inside the knob holder 37, making for use.

Figure 9:
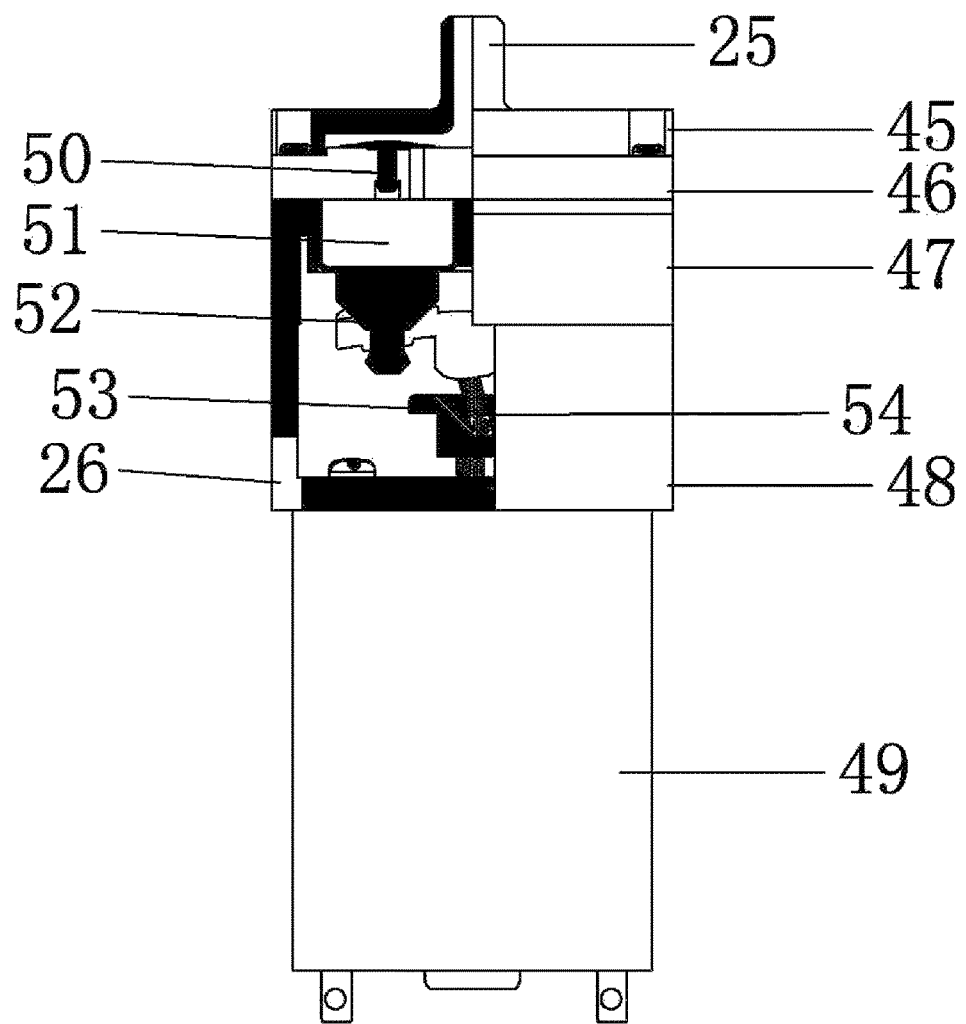
FIG. 9 is a sectional schematic of a pump body in the present invention.
Figure 10:
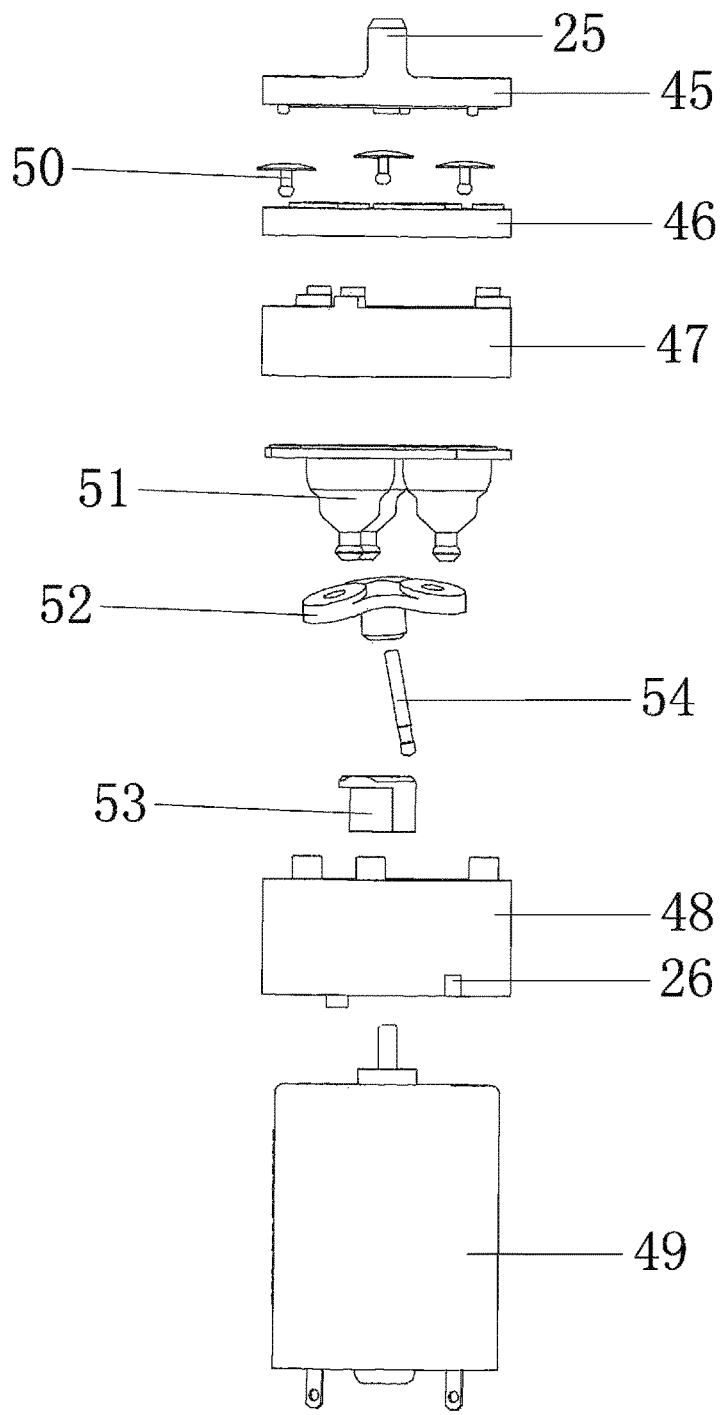
FIG. 10 is an exploded schematic of a pump body in the present invention.

As shown in FIG. 9 and FIG. 10, the pump body 22 comprises an upper housing 45, a support 46, a middle housing 47, a lower housing 48, an air outlet 25, a motor 49 and an air inlet 26. The upper housing 45, the support 46, the middle housing 47, the lower housing 48 and the motor 49 are installed in sequence from top to bottom. The air outlet 25 is located at the upper end of the upper housing 45. The air inlet 26 is located on a side face of the lower housing 48. The motor 49 is connected to the circuit board 36. A sealing gasket 23 is disposed on the upper end of the upper housing 45 and communicates with the air outlet 25. A valve 50 is disposed inside the support 46. A piston 51 and an eccentric gear 52 are disposed inside the middle housing 47 from top to bottom. One end of the piston 51 matches the bottom surface of the support 46 and another end is fixed on the eccentric gear 52. A connecting rod 53 is disposed inside the lower housing 48. One end of the connecting rod 53 is connected to the eccentric gear 52 through a spindle 54 and another end is connected to the motor 49.

When the motor 49 rotates, it drives the connecting rod 53 to rotate. Due to action of the spindle 54, the rotation of the connecting rod 53 will drive the eccentric gear 52 to swing. The swing of the eccentric gear 52 will drive the piston 51 fixed on the eccentric gear 52 to do reciprocating motion (move forward once, move backward once). While the piston 51 moves backward, it will suck ambient air into the pump body 22 from the air inlet 26. When the piston 51 moves forward, the valve 50 will be opened under the action of pressure and the ambient air will eject out from the air outlet 25. The continuous rotation of the motor 49 will make ambient air eject out continuously from the air outlet 25.

Working principle of the present invention: liquid essential oil is put into the essential oil bottle 3. The liquid essential oil is single liquid essential oil or compound liquid essential oil. According to the actually needed oil consumption and working time, the pump flow regulating knob 38, the timing knob 39 and the intermittent working time setting knob 40 are regulated and set. After the electric control element is started, the pump body 22 sucks ambient air into the pump body 22 from the air inlet 26. The ambient air ejects out from the air outlet 25, enters the swivel joint 16 via the sealing gasket 23 and the airflow reversing nozzle 27 in turn and sprays into the gasification chamber 12 via the air nozzle 15. When passing above the essential oil nozzle 13, the jet stream sprayed from the air nozzle 15 will form negative pressure above the essential oil nozzle 13. At the moment, the oil conduit 14 sucks the liquid essential oil out from the essential oil bottle 3 and sprays it into the gasification chamber 12 via the essential oil nozzle 13. Meanwhile, the jet stream sprayed can gasify the liquid essential oil sprayed from the essential oil nozzle 13 into tiny particles, which will become essential oil gas. When essential oil gas collides with the inner wall of the gasification chamber 12, part of it will become liquid and flow back to the essential oil bottle 3, while the remaining part of the essential oil gas enters the lower vortex body 17 and the upper vortex body 18 via the air inflow reflux hole, is discharged from the fragrance outlet and enters the fragrance channel 19 after it forms vortex gas, and then is diffused into the ambient air from the fragrance diffusion outlet 11, thereby completing the aroma diffusion process.

The present invention features simple structure, easy assembly and transport, easy operation, high working efficiency and high safety performance and significantly meets people's use requirements.

Still as shown in FIG. 1, FIG. 2, FIG. 3 and FIG. 4, the present invention further discloses an aroma diffuser, comprising: a base 1; a housing 2 mounted on the base; an essential oil bottle 3 accommodating essential oil; a gasification element for gasifying essential oil; a pump element communicating with the gasification element; and an electric control element for controlling the pump element. The open end of the essential oil bottle 3 is connected to and communicates with the lower end of the gasification element. The pump element is connected to the gasification element and the electric control element respectively.

Still as shown in FIG. 6, further, the gasification element comprises an air nozzle 15 and an essential oil nozzle 13. The air nozzle 15 comprises an air nozzle through-hole 30. The longitudinal central cross-section of the air nozzle through-hole 30 has an upper edge 31 and a lower edge 32, where:

The intersection between the extension line 33 of the upper edge and the centerline of the essential oil nozzle 13 is C;

The intersection between the extension line 34 of the lower edge and the centerline of the essential oil nozzle 13 is D;

The distance from intersection C to intersection D is H;

The included angle between the extension line 33 of the upper edge and the centerline of the essential oil nozzle 13 is Q;

The vertical distance from the extension line 33 of the upper edge to the extension line 34 of the lower edge is G;

The distance from intersection C to the end face of the essential oil nozzle 13 is M;

Where: the length of M is 0-2H and the included angle Q is an acute angle;

The relations among G, H and Q are $\cos(90-Q)=G/H$;

Thus it can be concluded that the positional relation between the air nozzle 15 and the essential oil nozzle 13 may be defined with Formula $\cos(90-Q)=G/H$. The relative setting of the positions of the air nozzle 15 and the essential oil nozzle 13 assures smooth gasification and high gasification efficiency.

Further, the included angle Q is 60-90.

Further, the intersection between the upper edge 31 and the extension line 33 of the upper edge is A. The distance from intersection A to intersection C is F. The length of F is 0.3 mm-10 mm.

Further, the intersection between the upper edge 31 and the extension line 33 of the upper edge is A. The distance from intersection A to intersection C is F. The length of F is 0.5 mm-2.0 mm.

Further, the inner diameter of the air nozzle through-hole 30 and the essential oil nozzle 13 is 0.4-0.8 mm.

Still as shown in FIG. 1, FIG. 2, FIG. 3 and FIG. 4, the present invention further discloses an aroma diffusing method, comprising:

Providing an aroma diffuser, comprising a housing 2, an essential oil bottle 3, a gasification element, a pump element and an electric control element;

Under action of the electric control element, importing ambient air into the air nozzle 15 of the gasification element through the pump body 22 of the pump element and forming jet stream;

Spraying the jet stream above the essential oil nozzle 13 of the gasification element via an air nozzle 15 to form negative pressure so as to suck liquid essential oil out from the essential oil bottle 3 and gasify the liquid essential oil into essential oil gas;

Diffusing essential oil gas to ambient air through a fragrance diffusion outlet 11 of the gasification element;

Further comprising: regulating flow and working time of the pump body 22 of the pump element according to actual need to achieve the required oil consumption and working time.

Further comprising: collecting the essential oil gas which becomes liquid essential oil when it collides with the inner wall of the gasification chamber of the gasification element 12 to the essential oil bottle 3.

Further comprising: forming the essential oil gas into vortex airstream through the lower vortex body 17 and the upper vortex body 18 of the gasification element, exporting the airstream out to the fragrance channel 19 of the gasification element, and then diffusing essential oil gas to ambient air through a fragrance diffusion outlet 11 of the gasification element.

Further, still as shown in FIG. 6, the air nozzle 15 comprises an air nozzle through-hole 30. The longitudinal central cross-section of the air nozzle through-hole 30 has an upper edge 31 and a lower edge 32, where:

The intersection between the extension line 33 of the upper edge and the centerline of the essential oil nozzle 13 is C;

The intersection between the extension line 34 of the lower edge and the centerline of the essential oil nozzle 13 is D;

The distance from intersection C to intersection D is H;

The included angle between the extension line 33 of the upper edge and the centerline of the essential oil nozzle 13 is Q;

The vertical distance from the extension line 33 of the upper edge to the extension line 34 of the lower edge is G;

The distance from intersection C to the upper end face of the essential oil nozzle 13 is M;

Where: the length of M is 0-2H, and the included angle Q is an acute angle;

The relations among C, H and Q are $\cos(90-Q)=G/H$;

The positional relation between the air nozzle 15 and the essential oil nozzle 13 may be defined with Formula cos (90-Q)=G/H. The relative setting of the positions of the air nozzle 15 and the essential oil nozzle 13 assures smooth gasification and high gasification efficiency.

Further, the intersection between the upper edge 31 and the extension line 33 of the upper edge is A. The distance from intersection A to intersection C is F. The length of F is 0.3 mm-10 mm.

The foregoing embodiments only represent the preferred embodiments of the present invention. Their descriptions are concrete and detailed, but they shall not be therefore understood as limitations to the scope of the present invention patent. It shall be noted that for those skilled in the art, various changes and modifications may be made to the embodiments without departing from the spirit of the present invention, such as: combinations of different features of the embodiments. All these shall be in the protective scope of the present invention.

What is claimed is:

1. An aroma diffuser with direct diffusion of essential oil, comprising a base, a housing mounted on the base and an electric control element disposed on the housing, wherein an essential oil bottle and a gasification element are also disposed on the housing; a pump element being disposed inside the housing; an open end of the essential oil bottle being connected to and communicating with a lower end of the gasification element; the pump element being connected to the gasification element and the electric control element respectively and communicating with the gasification element; a receiving groove is disposed on a side face of the housing; the essential oil bottle being received in the receiving groove after it is connected to the gasification element a guide rail and a window being disposed on an upper side wall and a bottom wall of the receiving groove respectively; an upper part of the gasification element having a guide slot corresponding to the guide rail; the guide rail matching with the guide slot.

2. The aroma diffuser according to claim 1, wherein the receiving groove comprises integrally formed upper receiving groove and lower receiving groove; the shape of the upper receiving groove corresponding to the gasification element; an upper end of the upper receiving groove stretching to the upper end face of the housing; the shape of the lower receiving groove corresponding to the essential oil bottle; the essential oil bottle and the gasification element being disposed inside the lower receiving groove and the upper receiving groove respectively after they are connected to each other; a guide rail and a window being disposed on a side wall and a bottom wall of the upper receiving groove respectively.

3. The aroma diffuser according to claim 2, wherein the gasification element comprises a gasification chamber body and a gasification chamber cover snapped onto the gasification chamber body; an upper part of the gasification chamber body having a guide slot corresponding to the guide rail; a lower end of the gasification chamber body being connected to an open end of the essential oil bottle; the right side face of the gasification chamber body being connected to the pump element; an upper end of the gasification chamber cover having a fragrance diffusion outlet.

4. The aroma diffuser according to claim 3, wherein the gasification chamber body comprises a gasification chamber, an essential oil nozzle, an oil conduit, an air nozzle and a swivel joint; the gasification chamber being connected to an open end of the essential oil bottle; the essential oil nozzle and the oil conduit being disposed at a lower end of the gasification chamber body; an upper end of the essential oil nozzle being located inside the gasification chamber and communicating with the gasification chamber; a lower end of the essential oil nozzle being connected to an upper end of the oil conduit and communicating with an upper end of the oil conduit; a lower end of the oil conduit stretching into the essential oil bottle, with its lower end face close to the bottom surface of the essential oil bottle, and communicating with the essential oil bottle; the swivel joint being disposed on the right side face of the gasification chamber body and connected to and communicating with the pump element; the air nozzle being disposed between the gasification chamber and the swivel joint and communicating with them respectively; the air nozzle being disposed in a tilted manner, with one side close to an upper end of the essential oil nozzle.

5. The aroma diffuser according to claim 4, wherein the air nozzle comprises an air nozzle through-hole; the air nozzle communicating with the gasification chamber and the swivel joint respectively through the air nozzle through-hole; the longitudinal central cross-section of the air nozzle through-hole having an upper edge and a lower edge, where:

the intersection between the upper edge and an extension line of the upper edge being A;

the intersection between an extension line of the upper edge and a centerline of the essential oil nozzle being C;

the intersection between an extension line of the lower edge and a centerline of the essential oil nozzle being D;

the distance from intersection A to intersection C being F;

the distance from intersection C to intersection D being H;

the distance from intersection C to end face of the essential oil nozzle being M;

the included angle between an extension line of the upper edge and a centerline of the essential oil nozzle being Q;

the length of F being 0.3 mm-10 mm, the length of M being 0-2H, and the included angle Q being an acute angle.

6. The aroma diffuser according to claim 5, wherein the vertical distance from an extension line of the upper edge to an extension line of the lower edge is G; the relations among H and Q being cos(90-Q)=G/H; the length of M being 0-2G/cos(90-Q).

7. The aroma diffuser according to claim 5, wherein the inner diameter of the air nozzle through-hole and the essential oil nozzle is 0.2-2.0 mm.

8. The aroma diffuser according to claim 4, wherein the gasification chamber body further comprises a vortex body; the vortex body comprising a lower vortex body and an upper vortex body; the lower vortex body and the upper vortex body are both disposed inside the gasification chamber; a lower end of the lower vortex body having an air inflow reflux hole; the lower vortex body communicating with the gasification chamber through the air inflow reflux hole; a lower end of the upper vortex body being disposed on an upper end of the lower vortex body; the upper vortex body communicating with the lower vortex body; an upper end of the upper vortex body having a fragrance outlet and being connected to the gasification chamber cover; a fragrance channel being formed between the upper vortex body and the gasification chamber cover; the upper vortex body communicating with the fragrance channel through the fragrance outlet; the fragrance channel communicating with the fragrance diffusion outlet.

9. The aroma diffuser according to claim 4, wherein the pump element comprises a front housing, a rear housing connected to the front housing in a snapped manner, a pump, a sealing gasket and an airflow reversing nozzle body; the pump body being disposed inside an cavity enclosed by the front housing and the rear housing; the pump body being connected to the electric control element; an upper end and a lower end of the pump body having an air outlet and an air inlet respectively; the sealing gasket being disposed on the upper end of the pump body and communicating with the air outlet; the airflow reversing nozzle body being disposed on the sealing gasket in a sleeved manner, communicating with the sealing gasket and having an airflow reversing nozzle; the airflow reversing nozzle passing through the front housing and the window in turn, connecting the swivel joint in an abutted manner and communicating with the swivel joint.

10. The aroma diffuser according to claim 9, wherein a cushion is disposed between the pump body and the front housing and between the pump body and the rear housing respectively.

11. The aroma diffuser according to claim 9, wherein the electric control element comprises a circuit board, a knob holder, a pump flow regulating knob, a timing knob and an intermittent working time setting knob; the pump flow regulator, the timer and the intermittent working time setter being disposed on the circuit board; the circuit board being connected to the pump body; the knob holder being fixed on the circuit board and disposed on the pump flow regulator, the timer and the intermittent working time setter in a sleeved manner; the pump flow regulating knob, the timing knob and the intermittent working time setting knob being all disposed on the knob holder, and connected to the pump flow regulator, the timer and the intermittent working time setter through the connecting shaft inside the knob holder.

12. The aroma diffuser according to claim 11, wherein the pump body comprises an upper housing, a support, a middle housing, a lower housing, an air outlet, a motor and an air inlet; the upper housing, the support, the middle housing, the lower housing and the motor being installed in sequence from top to bottom; the air outlet being located on an upper end of the upper housing; the air inlet being located on a side face of the lower housing; the motor being connected to the circuit board; a sealing gasket being disposed on the upper end of the upper housing and communicating with the air outlet; a valve being disposed inside the support; a piston and an eccentric gear being disposed inside the middle housing from top to bottom; one end of the piston clinging to the bottom surface of the support and another end being fixed on the eccentric gear; a connecting rod being disposed inside the lower housing; one end of the connecting rod being connected to the eccentric gear through a spindle and another end being connected to a motor.

13. The aroma diffuser according to claim 4, wherein bottom surface of the gasification chamber has an annular flange inlaid in an open end of the essential oil bottle; the gasification chamber communicating with the open end of the essential oil bottle through the annular flange.

14. The aroma diffuser according to claim 13, wherein a seal ring is disposed between the annular flange and an open end of the essential oil bottle.

15. The aroma diffuser according to claim 3, wherein a lower end of the gasification chamber body comprises a first thread; an open end of the essential oil bottle comprising a second thread matching the first thread; the first thread being connected to the second thread.

16. An aroma diffuser with direction diffusion of essential oil, comprising:
a base;
a housing mounted on the base;
an essential oil bottle for accommodating essential oil;
a gasification element for gasifying essential oil;
a pump element communicating with the gasification element;
an electric control element for controlling the pump element;
an open end of the essential oil bottle being connected to and communicating with a lower end of the gasification element; the pump element being connected to the gasification element and the electric control element respectively;
wherein the gasification element comprises an air nozzle and an essential oil nozzle; the air nozzle comprising an air nozzle through-hole; the longitudinal central cross-section of the air nozzle through-hole having an upper edge and a lower edge, where:
the intersection between an extension line of the upper edge and a centerline of the essential oil nozzle being C;
the intersection between an extension line of the lower edge and the centerline of the essential oil nozzle being D;
the distance from intersection C to intersection D being H;
the included angle between the extension line of the upper edge and the centerline of the essential oil nozzle being Q;
the vertical distance from the extension line of the upper edge to the extension line of the lower edge being G;
the distance from intersection C to the end face of the essential oil nozzle being M;
where: the length of M being 0-2H and the included angle Q being an acute angle;
the relations among G, H and Q being cos(90-Q)=G/H;
the positional relation between the air nozzle and the essential oil nozzle being defined by formula cos(90-Q)=G/H.

17. The aroma diffuser according to claim 16, wherein the included angle Q is 60-90°.

18. The aroma diffuser according to claim 16, wherein the intersection between the upper edge and an extension line of the upper edge is A; the distance from intersection A to intersection C being F; the length of F being 0.3 mm-10 mm.

19. The aroma diffuser according to claim 16, wherein the intersection between the upper edge and an extension line of the upper edge is A; the distance from intersection A to intersection C being F; the length of F being 0.5 mm-2.0 mm.

20. The aroma diffuser according to claim 16, wherein the inner diameter of the air nozzle through-hole and the essential oil nozzle is 0.2-2.0 mm.

21. The aroma diffuser according to claim 16, wherein the inner diameter of the air nozzle through-hole and the essential oil nozzle is 0.4-0.8 mm.

22. An aroma diffusing method, comprising:
providing an aroma diffuser, comprising a housing, an essential oil bottle, a gasification element, a pump element and an electric control element;
under action of the electric control element, importing ambient air into the air nozzle of the gasification element through the pump body of the pump element and forming jet stream;
spraying the jet stream above the essential oil nozzle of the gasification element via an air nozzle to form negative pressure so as to suck liquid essential oil out from the essential oil bottle and gasify the liquid essential oil into essential oil gas;

diffusing essential oil gas to ambient air through a fragrance diffusion outlet of the gasification element;

forming the essential oil gas into vortex airstream through the lower vortex body and the upper vortex body of the gasification element, exporting the airstream out to the fragrance channel of the gasification element, and then diffusing essential oil gas to ambient air through the fragrance diffusion outlet of the gasification element.

23. The aroma diffusing method according to claim 22 further comprising: regulating flow and working time of the pump body of the pump element according to actual need to achieve the required oil consumption and working time.

24. The aroma diffusing method according to claim 22 further comprising: collecting the essential oil gas which becomes liquid essential oil when it collides with the inner wall of a gasification chamber of the gasification element to the essential oil bottle.

25. The aroma diffusing method according to claim 22 further comprising: collecting the essential oil which becomes liquid essential oil when it passes the lower vortex body and the upper vortex body to the essential oil bottle.

26. The aroma diffusing method according to claim 22, wherein the air nozzle comprises an air nozzle through-hole; the longitudinal central cross-section of the air nozzle through-hole having an upper edge and a lower edge, where:

the intersection between an extension line of the upper edge and a centerline of the essential oil nozzle being C;

the intersection between an extension line of the lower edge and the centerline of the essential oil nozzle being D;

the distance from intersection C to intersection D being H;

the included angle between the extension line of the upper edge and the centerline of the essential oil nozzle being Q;

the vertical distance from the extension line of the upper edge to the extension line of the lower edge being G;

the distance from intersection C to the end face of the essential oil nozzle being M;

where: the length of M being 0-2H and the included angle Q being an acute angle;

the relations among C, H and Q being cos(90-Q)=G/H;

the positional relation between the air nozzle and the essential oil nozzle being defined by formula cos(90-Q)=G/H.

27. The aroma diffusing method according to claim 26, wherein the intersection between the upper edge and an extension line of the upper edge is A; the distance from intersection A to intersection C being F; the length of F being 0.3 mm-10 mm.

* * * * *